(12) United States Patent
Yokoi et al.

(10) Patent No.: US 9,173,754 B2
(45) Date of Patent: Nov. 3, 2015

(54) STENT

(75) Inventors: Yoshihiko Yokoi, Tokyo (JP); Yasushi Hashimoto, Utsunomiya (JP); Akira Saito, Utsunomiya (JP)

(73) Assignee: MANI, Inc., Utsunomiya-shi, Tochigi (JP)

( * ) Notice: Subject to any disclaimer, the term of this patent is extended or adjusted under 35 U.S.C. 154(b) by 388 days.

(21) Appl. No.: 13/060,395

(22) PCT Filed: Aug. 28, 2009

(86) PCT No.: PCT/JP2009/065057
§ 371 (c)(1),
(2), (4) Date: Sep. 26, 2011

(87) PCT Pub. No.: WO2010/024380
PCT Pub. Date: Mar. 4, 2010

(65) Prior Publication Data
US 2012/0016459 A1    Jan. 19, 2012

(30) Foreign Application Priority Data
Aug. 29, 2008    (JP) .................................. 2008-220876

(51) Int. Cl.
*A61F 2/82*    (2013.01)
*A61F 2/89*    (2013.01)

(52) U.S. Cl.
CPC ........... *A61F 2/89* (2013.01); *A61F 2250/0018* (2013.01)

(58) Field of Classification Search
CPC ....................................................... A61F 2/82
USPC ............................................... 623/1.16, 1.15
See application file for complete search history.

(56) References Cited

U.S. PATENT DOCUMENTS

| 5,816,807 A | 10/1998 | Matsutani et al. |
| 5,843,167 A | 12/1998 | Dwyer et al. |
| 7,294,214 B2 | 11/2007 | Craig |

FOREIGN PATENT DOCUMENTS

| JP | 3140508 B2 | 3/1993 |
| JP | 8299456 A | 11/1996 |
| JP | 3375771 B2 | 2/2003 |
| JP | 2006512972 A | 4/2006 |
| WO | 2008013042 A1 | 1/2008 |
| WO | 2008015873 A1 | 2/2008 |

OTHER PUBLICATIONS

International Search Report issued in corresponding International Application No. PCT/JP2009/065057.

*Primary Examiner* — Thomas J Sweet
*Assistant Examiner* — Matthew Schall
(74) *Attorney, Agent, or Firm* — Shlesinger, Arkwright & Garvey LLP

(57) ABSTRACT

A stent including a plurality of loop stents connected by struts so that it bends uniformly as a whole.

A stent A including a plurality of loop stents 2 connected by a plurality of struts 3, the loop stents 2 each formed of a stent main wire 1 folded into a zigzag shape and joined at its ends, wherein the bending strength of each strut 3 is larger than the bending strength of the stent main wire 1.

6 Claims, 2 Drawing Sheets

STENT

TECHNICAL FIELD

The present invention relates to a stent to be used for treatment of internal tubular tissues represented by blood vessels and more particularly, to a stent including a plurality of loop stents connected via struts.

BACKGROUND ART

There are many tubular tissues including blood vessels in a body, and blood vessels, for example, can have disorders such as stenosis, occlusion, aneurysm, and varix. In particular, the aneurysm is a serious disorder that causes massive bleeding when ruptured, for which therefore immediate treatment is necessary. Accordingly, various kinds of instruments have been developed to perform effective treatment.

Recently, a metal cylindrical instrument called stent has been often used in the treatment of a stenosis site or an aneurysm of a blood vessel. In the case of the treatment of a stenosis site, for example, a stent is conveyed to an affected area while being contained in a sheath or a catheter (hereinafter, referred to as sheath) and once the stent reaches the affected area, separated from the sheath, expanded by means of a balloon to expand the stenosis site, and indwelled to treat the stenosis site. In the case of the treatment of an aortic aneurysm, a stent graft obtained by coating a stent with an artificial blood vessel is indwelled inside of the aneurysm and opposed to the pressure of blood thereby to prevent the pressure from acting on the aneurysm for the treatment.

Examples of the stent include the one constituted solely by loop stents each formed into a cylindrical shape as a whole by folding a round bar-shaped wire into a zigzag shape and joining ends of the wire together. Another example of the stent is formed by arranging a plurality of loop stents according to the curvature of the affected area where the stent is to be indwelled, and connecting the loop stents together via a plurality of linear members called struts so as to maintain the shape of the curvature (see, for example, Patent Document 1).

The above-mentioned stents are each conveyed to the affected area while being contracted and inserted in a sheath and once the stent reaches the affected area and then is separated from the sheath, expanded by a balloon or expands by itself. In the stent formed by connecting a plurality of loop stents by struts, in particular, the arrangement of the respective loop stents along the curvature is maintained by the struts, and the loop stents expanded contact with the inner wall surface of the affected area. Thereby, the stent can treat an applicable tubular tissue, for example, a blood vessel.
[Patent Document 1] Japanese Patent No. 4064724

DISCLOSURE OF THE INVENTION

Problems to be Solved by the Invention

In the case of the stent formed by connecting a plurality of loop stents by struts, it is general to use the same material for the struts and stent main wires that form the loop stents. Since the loop stents are formed by folding the stent main wires into a zigzag shape, the bending strength of the cylindrical loop stents themselves is increased to be larger than the bending strength of the stent main wires by themselves. It is also general to use approximately two or three struts to connect adjacent loop stents together.

The loop stent part and the strut part that form the stent is therefore different in the bending strength to generate variation of bending depending on the part when the stent is applied to a curved part of the affected area. That is, the bending strength of the struts is so small that the struts themselves bend too much to prevent the stent main wires and the struts from bending uniformly around the connection part, thereby disadvantageously loosing the shape of the stent as a whole. Derived from the disadvantage, the stent, having the struts and the stent main wires not bending uniformly, may not closely follow the inner wall surface of a blood vessel wall or the like, or may get into the aneurysm.

It is an object of the present invention to provide a stent including a plurality of loop stents by a plurality of struts so that the stent bends uniformly as a whole.

Means for Solving the Problems

In order to overcome the above-described disadvantages, a stent according to the present invention includes a plurality of loop stents connected via a plurality of struts, the loop stents each formed of a stent main wire folded into a zigzag shape and joined at its ends, wherein the bending strength of each strut is larger than the bending strength of the stent main wire.

Effects of the Invention

In the stent according to the present invention, the bending strength of the strut is larger than the bending strength of the stent main wire that forms each of the loop stents, and therefore, when the stent is applied to a curved part of an affected area, the extent of the bending of the struts and the extent of the bending of the loop stents can be almost equal, or the extent of the bending of the struts can be slightly smaller than the extent of the bending of the loop stents.

Thus, when applied to a curved tubular tissue, the stent does not generate variation of the extent of the bending depending on the part, because the loop stents and the struts in the stent bend almost uniformly.

DESCRIPTION OF REFERENCE NUMERALS

A Stent
1 Stent main wire
2 Loop stent
3 Strut

BEST MODE FOR CARRYING OUT THE INVENTION

Figure 1:
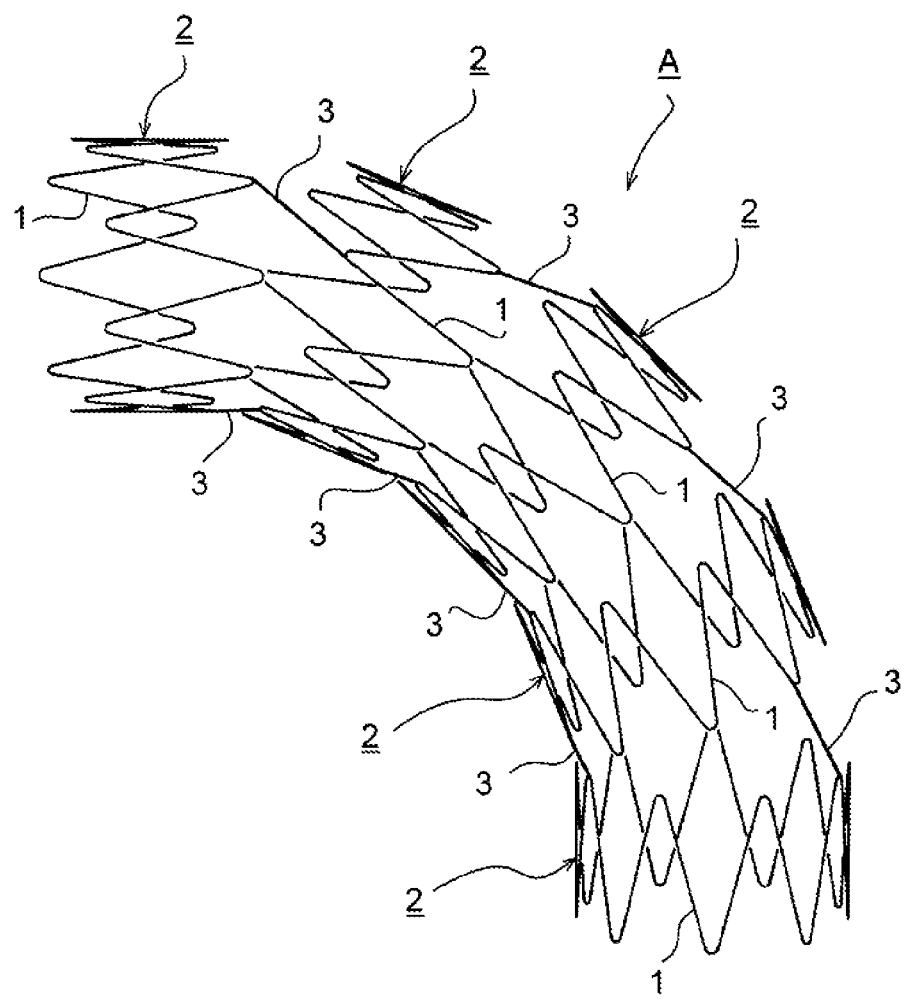
FIG. 1 is a drawing illustrating a stent formed by connecting a plurality of loop stents together by struts.
Figure 2:
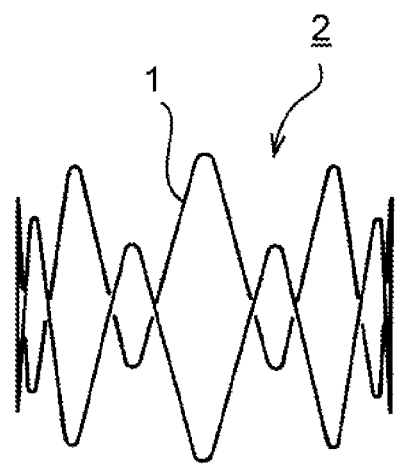
FIG. 2 is a drawing illustrating a structure of a loop stent.

Hereinafter, a stent according to the present invention will be described with reference to the drawings. FIG. 1 is a drawing illustrating a stent formed by connecting a plurality of loop stents together by struts. FIG. 2 is a drawing illustrating a structure of a loop stent.

A stent A according to the present invention is to be applied to tubular tissues including blood vessels in a living body, and has a function of reinforcing a tubular tissue in an affected area while being indwelled in the affected area when the tubular tissue has a disorder such as stenosis or occlusion, in particular, when a blood vessel has an aneurysm or a varix.

The stent A according to this embodiment is formed by bending a metal round bar-shaped wire (stent main wire 1)

into a zigzag shape and butt welding the end faces of the stent main wire 1 together to form a loop stent 2 in a cylindrical shape as illustrated in FIG. 2, and arranging a plurality of loop stents 2 according to the curvature of an affected area where the stent is to be indwelled and connecting adjacent loop stents 2 together by at least two metal struts 3 having a bending strength larger than the bending strength of the stent main wire 1 as illustrated in FIG. 1.

As described above, the loop stent 2 is formed by bending the stent main wire 1 into a zigzag shape and joining the ends thereof together. The method for joining the ends of the stent main wire 1 is not particularly limited, and the ends can be butt welded or inserted in a sleeve and swaged to be joined. Since both the ends of the stent main wire 1 are joined so that they cannot relatively rotate as described above, the loop stent 2 does not deform when contracted and inserted in a sheath, and therefore can precisely return to the original shape when separated from the sheath and expanded.

When the ends of the stent main wire 1 are butt welded in the formation of the loop stent 2, or when each strut 3 is welded to the stent main wire 1 in the formation of the stent A, the welded part and the vicinity thereof decrease in strength, where an austenite structure that has extended into the shape of fiber is affected by heat of the weld to be a coarsened granular structure. It is therefore preferable to provide a protection pipe (not illustrated) to the welded part and the vicinity thereof to reinforce areas deteriorated due to the weld with the protection pipe.

The length and the thickness of the stent A are not limited, and the stent A is formed so as to have the most suitable length and curvature according to the affected area where the stent A is to be indwelled by connecting a plurality of loop stents 2 formed so as to have a thickness according to the thickness of the affected area where the stent A is to be indwelled by the struts 3.

The bending strength of the strut 3 is larger than the bending strength of the stent main wire 1. The difference between the bending strength of the strut 3 and the bending strength of the stent main wire 1 is not particularly limit and determined according to conditions such as the thickness and the curvature of the affected are where the stent A is to be indwelled, and the magnitude of the acting force generated by the bloodstream, for example. Preferably, the difference between the bending strength of the strut 3 and the bending strength of the stent main wire 1 is in a range of 20 g·cm to 200 g·cm, and more preferably in a range of 50 g·cm to 150 g·cm, when expressed in bending torque. Particularly, the bending strength of the strut 3 is preferably in a range of 350 g·cm to 450 g·cm, and the bending strength of the stent main wire 1 is preferably in a range of 150 g·cm to 430 g·cm.

The bending strength of the strut 3 and the bending strength of the stent main wire 1 are determined according to the allowable bending stress, the cross-sectional shape, and the like of the material to use. In particular, the stent main wire 1 is formed of a round bar-shaped wire. As a result, the bending strength of the strut 3 can be larger than the bending strength of the stent main wire 1 even when the cross-sectional shape of the strut 3 is, for example, rectangular and a direction of its long side is disposed in a bending direction.

When the cross-sectional shape of the strut 3 is as described above, the bending strength has directional properties. Accordingly, such a shape may not be preferable for some curvatures of the affected area where the stent is to be indwelled. It is therefore preferable that the cross-sectional shape of the strut 3 is also round, which does not have the directional properties.

When the strut 3 is formed of a wire having a round cross section, a material having an allowable bending stress larger than that of the material of the stent main wire 1 can be used for the strut 3 in order to obtain a bending strength of the strut 3 larger than the bending strength of the stent main wire 1, assuming that the materials have the same thickness. In this case, different materials can be used for the stent main wire 1 and the strut 3, among which a material having a larger allowable bending stress can be used for the strut 3 and a material having a smaller allowable bending stress can be used for the stent main wire 1. Although the description is on the assumption that the materials have the same thickness, it is sufficient that the materials have substantially the same thickness, because it is impossible that they have exactly the same thickness.

Since the stent is to be indwelled in a body, in particular, it is required to have applicability to a human body and capability of maintaining stable applicability over a long term. Examples of the material to be used for the stent with such requirements include wires of a metal such as stainless steel having appropriate degrees of elasticity and flexibility, and being free from a risk of adversely affecting living tissues; and shape memory alloy composed of Ni—Ti alloy. These materials can be selectively used. In addition, the materials are preferably selected in view of workability including bendability in the formation of the loop stent and bondability between the loop stent and the strut.

As an example of such materials there may be mentioned an austenite stainless steel, which is highly reliable in terms of biocompatibility. In particular, an austenite stainless steel wire, when having a predetermined diameter and cold-drawn at a predetermined section reduction (processing rate) to show work-hardening and have its structure extended in the shape of fiber, is preferable as being capable of maintaining appropriate degrees of elasticity and flexibility, and having high toughness over a longer term.

Besides, it is possible to vary the allowable bending stress of a wire of an austenite stainless steel such as SUS316L and SUS304 by appropriately setting the processing rate when cold-drawing the wire.

Furthermore, it is possible to vary the allowable bending stress by selecting the kind of the austenite stainless steel. For example, SUS316L has an allowable bending stress of approximately 293 g·cm to 312 g·cm (in bending torque; the same applies hereinafter), and SUS304 has an allowable bending stress of approximately 397 g·cm to 412 g·cm. Both the materials can be preferably used as the material of the stent main wire or the material of the strut.

In the present invention, the structure for connecting the loop stent and the strut is not particularly limited, and a structure connecting them by superposing an end of the strut on the stent main wire for forming the loop stent, and inserting the superposed part in a joint pipe and swaging the same; or a structure connecting them by weld can be selectively adopted.

In order to stabilize the shape of the stent, a plurality of struts is needed, but the number of struts is not particularly limited. Preferably, an appropriate number of struts are adopted in view of balance of the strength with the loop stent.

FIRST EMBODIMENT

In this embodiment, a stent main wire 1 and a strut 3 are individually formed of a material obtained by cold-drawing an SUS316L, which is an austenite stainless steel, wire so that the structure thereof is extended into the shape of fiber and the material is work-hardened to have improved mechanical properties.

Specifically, in this embodiment, SUS316L wires having different thicknesses are cold-drawn at different processing rates until the wires have the same thickness and different tensile strengths, thereby varying the degree of work-hardening to achieve different allowable bending stresses. Then, the material processed at a larger processing rate and having a larger allowable bending stress (tensile strength; the same applies hereinafter) is used as the strut 3, and the material processed at a smaller processing rate and having a smaller allowable bending stress is used as the stent main wire 1. Although the description is on the assumption that the materials are cold-drawn until they have the same thickness, it is sufficient that the materials have substantially the same thickness, because it is impossible that they have exactly the same thickness.

In this embodiment, the thickness of the stent main wire 1 and the strut 3 is 0.5 mm, the allowable bending stress of the stent main wire 1 is 293 g·cm to 312 g·cm, and the allowable bending stress of the strut 3 is 397 g·cm to 412 g·cm.

A stent A is formed as described above, in which the bending strength of the strut 3 is larger than the bending strength of the stent main wire 1, and therefore has the bending strength uniformed as a whole. Thus, when the stent A is applied to a curved part of an affected area, bending does not concentrate on the strut 3 to allow achievement of bending as uniform as possible.

The tensile strength is not limited, but the stent needs to bend uniformly when applied to a curved part of an affected area and needs to be free from variation of the extent of the bending depending on the part. Accordingly, the ratio of the tensile strength between the stent main wire 1 and the strut 3 (tensile strength of stent main wire 1:tensile strength of strut 3) is preferably in a range of 1:1.03 to 1:1.3. Particularly, the tensile strength of the stent main wire 1 is preferably around 1700 N/mm$^2$ to 2500 N/mm$^2$, and the tensile strength of the strut 3 is preferably around 1751 N/mm$^2$ to 3250 N/mm$^2$.

SECOND EMBODIMENT

In this embodiment, a stent main wire 1 is formed of a material obtained by cold-drawing an SUS316L wire to have a thickness of 0.5 mm, and a strut 3 is formed of a material obtained by cold-drawing an SUS304 wire to have a thickness of 0.5 mm.

In this embodiment, the allowable bending stress of the stent main wire 1 is 293 g·cm to 312 g·cm, and the allowable bending stress of the strut 3 is 397 g·cm to 412 g·cm.

A stent A is formed as described above, in which the bending strength of the strut 3 is larger than the bending strength of the stent main wire 1, and therefore has the bending strength uniformed as a whole. Thus, when the stent A is applied to a curved part of an affected area, bending does not concentrate on the strut 3 to allow achievement of bending as uniform as possible.

The tensile strength is not limited, but the stent needs to bend uniformly when applied to a curved part of an affected area and needs to be free from variation of the extent of the bending depending on the part. Accordingly, the ratio of the tensile strength between the stent main wire 1 and the strut 3 (tensile strength of stent main wire 1:tensile strength of strut 3) is preferably in a range of 1:1.03 to 1:1.3. Particularly, the tensile strength of the stent main wire 1 is preferably around 1700 N/mm$^2$ to 2500 N/mm$^2$, and the tensile strength of the strut 3 is preferably around 1751 N/mm$^2$ to 3250 N/mm$^2$.

INDUSTRIAL APPLICABILITY

The stent A of the present invention bends as uniformly as possible when external force in the bending direction acts thereon. Thus, the stent A can stably follow a subtle difference in curvature which is likely when the stent A is indwelled in an affected area, and therefore can be used for tubular tissues represented by blood vessels.

The invention claimed is:

1. A stent comprising a plurality of loop stents connected via a plurality of struts, the loop stents each formed of a stent main wire folded into a zigzag shape and joined at its ends,
    wherein the difference between the bending strength of the strut and the bending strength of the stent main wire is in a range of 20 g·cm to 200 g·cm when expressed in bending torque, the bending torque of the strut is in a range of 350 g·cm to 450 g·cm, and the bending torque of the stent main wire is in a range of 150 g·cm to 430 g·cm, so that the stent has a uniform bending strength.

2. The stent according to claim 1, wherein the difference between the bending strength of the strut and the bending strength of the stent main wire is in a range of 50 g·cm to 150 g·cm when expressed in bending torque.

3. The stent according to claim 1, wherein a material of the stent main wire and a material of the strut have substantially the same thickness and round cross sections, and the strut has an allowable bending stress larger than the stent main wire.

4. The stent according to claim 2, wherein a material of the stent main wire and a material of the strut have substantially the same thickness and round cross sections, and the strut has an allowable bending stress larger than the stent main wire.

5. The stent according to claim 1, wherein the stent main wire and the strut are formed of wires which are made of austenite stainless steels and are cold-drawn so that their structures are extended into the shape of fiber, the wire forming the strut has a thickness larger than the wire forming the stent main wire, and the wires are cold-drawn at different processing rates until the stent main wire and the strut have substantially the same thickness and different tensile strengths to achieve different allowable bending stresses.

6. The stent according to claim 2, wherein the stent main wire and the strut are formed of wires which are made of austenite stainless steels and are cold-drawn so that their structures are extended into the shape of fiber, the wire forming the strut has a thickness larger than the wire forming the stent main wire, and the wires are cold-drawn at different processing rates until the stent main wire and the strut have substantially the same thickness and different tensile strengths to achieve different allowable bending stresses.

* * * * *